United States Patent
Asahina et al.

(10) Patent No.: US 7,913,571 B2
(45) Date of Patent: Mar. 29, 2011

(54) APPARATUS FOR ESTIMATING RESIDUAL LIFE OF BLASTING VESSEL, METHOD OF ESTIMATING RESIDUAL LIFE, AND BLASTING FACILITY

(75) Inventors: Kiyoshi Asahina, Kobe (JP); Ryusuke Kitamura, Kobe (JP); Toshio Hamada, Kobe (JP); Takao Shirakura, Tokyo (JP)

(73) Assignee: Kobe Steel, Ltd., Hyogo (JP)

( * ) Notice: Subject to any disclaimer, the term of this patent is extended or adjusted under 35 U.S.C. 154(b) by 207 days.

(21) Appl. No.: 11/887,219

(22) PCT Filed: Feb. 28, 2006

(86) PCT No.: PCT/JP2006/303665
§ 371 (c)(1),
(2), (4) Date: Sep. 27, 2007

(87) PCT Pub. No.: WO2006/112152
PCT Pub. Date: Oct. 26, 2006

(65) Prior Publication Data
US 2009/0013762 A1 Jan. 15, 2009

(30) Foreign Application Priority Data
Apr. 8, 1920 (JP) ................................ 2005-112426

(51) Int. Cl.
*G01N 3/32* (2006.01)
(52) U.S. Cl. .......................................... 73/808; 73/760
(58) Field of Classification Search ............ 73/760–860, 73/167, 808
See application file for complete search history.

(56) References Cited

U.S. PATENT DOCUMENTS

| 3,735,704 | A | * | 5/1973 | Livingston .................... 102/301 |
| 3,772,958 | A | | 11/1973 | Mullarkey |
| 3,853,539 | A | * | 12/1974 | Yoshiki et al. .................. 75/378 |
| 3,914,996 | A | | 10/1975 | Davis et al. |
| 5,272,746 | A | * | 12/1993 | Isobe et al. ....................... 378/72 |
| 5,613,453 | A | | 3/1997 | Donovan |
| 5,884,569 | A | | 3/1999 | Donovan |

(Continued)

FOREIGN PATENT DOCUMENTS
JP 07-128000 11/1993
(Continued)

OTHER PUBLICATIONS

An Office Action from Russian Patent Office regarding Russian Patent Application No. 2007141300/20(045204) dated Oct. 31, 2008 in Russian with English translation.
Office Action from the Federal Service on Industrial Property, Patents, and Trademarks in English and Russian dated Mar. 30, 2009.
International Search Report for PCT/JP2006/303665 dated May 2, 2006.

*Primary Examiner* — Max Noori
(74) *Attorney, Agent, or Firm* — Stites & Harbison, PLLC; Juan Carlos A. Marquez, Esq.

(57) ABSTRACT

The present invention aims at estimating a residual life of a blasting vessel. For the estimation, a strain gauge 30 is attached to a blasting vessel 10. The strain gauge 30 measures high-frequency repetitive strain caused in the blasting chamber 10 in each explosion. Strain waveform data obtained with the strain gauge 30 is analyzed to calculate the cumulative degree of fatigue damage due to a high-frequency repetitive load applied to the blasting vessel 10 in each explosion. A residual life of the blasting vessel 10 is estimated on the basis of a cumulative value of the cumulative degrees of fatigue damage.

10 Claims, 4 Drawing Sheets

U.S. PATENT DOCUMENTS

| | | | |
|---|---|---|---|
| 5,975,754 A * | 11/1999 | Groth et al. | 374/45 |
| 6,067,890 A * | 5/2000 | Thiesen et al. | 89/41.03 |
| RE36,912 E | 10/2000 | Donovan | |
| 6,173,662 B1 | 1/2001 | Donovan | |
| 6,354,181 B1 | 3/2002 | Donovan | |
| 6,647,851 B2 | 11/2003 | Donovan | |
| 7,121,183 B2 * | 10/2006 | Waid et al. | 89/1.11 |
| 7,277,822 B2 * | 10/2007 | Blemel | 702/183 |
| 7,402,800 B2 * | 7/2008 | Delvigne et al. | 250/303 |
| 7,412,870 B2 * | 8/2008 | Brankov | 73/12.11 |
| 2005/0192472 A1 | 9/2005 | Quimby et al. | |
| 2009/0081928 A1 * | 3/2009 | Fujiwara et al. | 451/38 |

FOREIGN PATENT DOCUMENTS

| | | |
|---|---|---|
| JP | 07-208899 | 1/1994 |
| JP | 09-133623 | 5/1995 |
| JP | 2001066228 | 8/1999 |
| JP | 2002-022632 | 7/2000 |
| RU | 2 104 474 C1 | 8/1995 |
| RU | 2154255 C2 | 8/1995 |
| RU | 2 175 120 C2 | 4/1999 |

* cited by examiner

APPARATUS FOR ESTIMATING RESIDUAL LIFE OF BLASTING VESSEL, METHOD OF ESTIMATING RESIDUAL LIFE, AND BLASTING FACILITY

TECHNICAL FIELD

The present invention relates to an apparatus and method of estimating a residual life of a vessel in which a hazardous substance, an explosive ordnance, or the like is exploded, and more specifically to a blasting facility equipped with the apparatus for estimating a residual life.

BACKGROUND ART

As a known structure of ammunition for military use, which is employed in chemical weapons or the like (for example, a bullet, a bomb, a mine, and an underwater mine), a busting charge and a chemical agent hazardous to humans are filled in a steel bomb. Examples of the chemical agent include a mustard gas, a lewisite, and the like, which are hazardous to humans.

One known method of treating such chemical weapons or hazardous substances such as organic halogens (for example, a method of rendering these harmless) is by explosion. Such a method of treating ammunition for military use through explosion is applicable to disposal of ammunition that cannot be easily dismantled due to aging degradation, aged deterioration, etc. as well as to disposal of ammunition that is well preserved because of not requiring disassembly. In addition, this method is advantageous in that the chemical agent can be almost completely decomposed due to ultrahigh temperature and pressure upon explosion. Such a treatment method is disclosed in Patent Document 1.

An explosion is carried out in a sealed blasting vessel from the viewpoints of preventing leakage of a chemical agent to the outside and of suppressing an influence of sounds or vibrations involved in the explosion on the surrounding environments in many cases. Further, if the explosion is performed with the blasting vessel kept under vacuum, and an internal pressure of the blasting vessel is kept negative even after the explosion, the chemical agent can be prevented from leaking to the outside with higher reliability.

[Patent Document 1] Japanese Unexamined Patent Application Publication No. 7-208899.

DISCLOSURE OF INVENTION

The background art involves the following problems.

If the explosion is performed with the method disclosed in Patent Document 1, the blasting vessel suffers very high load involved in explosion of a chemical bomb as an object to be treated. Hence, the blasting vessel is generally made of a hard metal material not to deform or break down upon the explosion and is designed to withstand such an impact shock. Nevertheless, metal fatigue of the blasting vessel is accumulated by repeating the explosion (that is, fatigue damage is accumulated). When the cumulative degree of fatigue damage finally reaches a threshold limit value unique to the material, the vessel is cracked and then broken. Thus, in order to efficiently perform explosion plural times with the same blasting vessel, it is necessary to constantly check the degree of metal fatigue of the blasting vessel.

However, in actual operations of a blasting facility, the facility should be run in such a state that a residual life of a blasting vessel is unknown. In present circumstances, it is very difficult to schedule the operations. As conceivable means for managing the operation schedule, a maintenance check is frequently performed while stopping the explosion, or the blasting vessel is tested by various nondestructive inspection methods not to miss a sign of breakage due to metal fatigue such as cracks. The frequent maintenance check and test lead to considerable reduction in disposal capacity of the blasting facility and an increase in running costs.

Incidentally, in recent years, the Japanese government ratifies the Chemical Weapons Convention, and is obliged by the convention to dispose of chemical weapons abandoned on the China by the Imperial Japanese Army. As is estimated from "Outline of Disposal of Chemical Weapons Abandoned on the China by Imperial Japanese Army" released on October, 2002 by the ACW office, about 700000 chemical weapons of various kinds are abandoned over the China. A facility for disposing of the weapons should be designed to have an ability to dispose of about 120 weapons per hour with an aim to dispose of 700000 chemical weapons in three years. Accordingly, the importance of how to increase a disposal capacity of the blasting facility has been recently recognized.

The present invention has been accomplished with a view to solving the above problems. The present invention provides an apparatus for estimating a residual life of a blasting vessel in which an object to be treated is exploded, including: means for quantitatively evaluating the degree of fatigue damage of the blasting vessel upon each explosion; and means for calculating an estimated value of a residual life of the blasting vessel on the basis of the evaluation.

Further, the present invention provides a blasting facility, including: a blasting vessel in which an object to be treated is exploded; and the apparatus for estimating a residual life of a blasting vessel.

Further, the present invention provides a method of estimating a residual life of a blasting vessel in which an object to be treated is exploded, including: quantitatively evaluating the degree of fatigue damage of the blasting vessel upon each explosion; and estimating a residual life of the blasting vessel on the basis of the evaluation.

According to the present invention, it is possible to run a blasting facility while estimating a residual life of a blasting vessel all the time. The estimation considerably facilitates appropriate scheduling of operations, and prevents reduction in disposal capacity or increase in running costs.

BEST MODE FOR CARRYING OUT THE INVENTION

A preferred embodiment of the present invention will be described with reference to the accompanying drawings.

Figure 2:
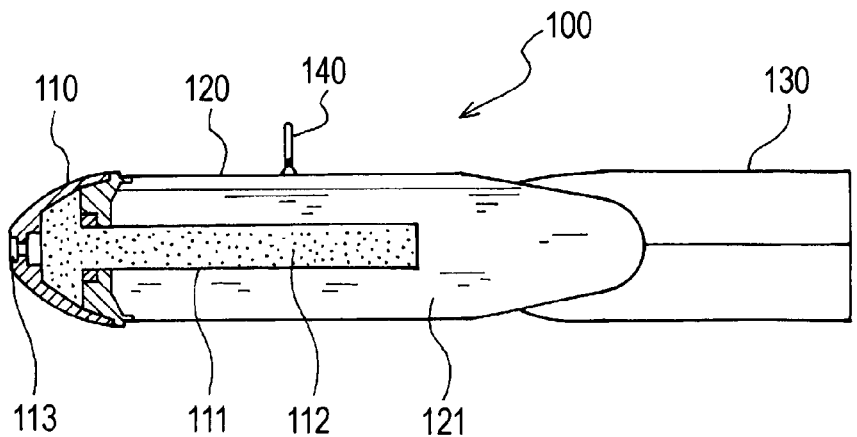
FIG. 2 is a sectional view of a schematic structural example of a chemical bomb to be exploded in the facility.

FIG. 2 is a sectional view of a chemical bomb as a chemical weapon as an example of an explosive ordnance to be exploded according to an embodiment of the present invention.

A chemical bomb (explosive ordinance) 100 of FIG. 2 includes a warhead 110, a burster 111, a bomb case 120, and a posture control wing 130.

The burster 111 extends backward from the warhead 110 and contains a bursting charge (explosive) 112. A fuse 113 for bursting the bursting charge 112 in the burster 111 is provided in the warhead 110.

The bomb case 120 is connected to the warhead 110 with the burster 111 contained therein. A liquid chemical agent (hazardous substance) 121 is filled in the bomb case 120. The posture control wing 130 is provided at an end opposing the warhead 110 out of ends in an axial direction of the bomb base 120, and functions to control a posture of the chemical bomb 100.

Incidentally, a ring 140 for suspending the chemical bomb 100 is provided in an upper portion of the bomb case 120, and the chemical bomb is set in an airplane while being suspended.

A target explosive of this embodiment is all or a part of the chemical bomb 100 containing at least the explosive 112 and the chemical agent 121 as described above. However, the present invention is not applicable only to explosion of the chemical bomb 100 filled with the chemical agent 121 as described above. For example, the present invention is applicable to explosion of the bursting charge alone in a blasting vessel after disassembling the chemical bomb.

For example, the present invention is applicable to explosion of an explosive for military use such as TNT, a picric acid, or ROX, and explosion of an erosive agent such as a mustard gas or lewisite, a sneezing gas such as DC and DA, and a chemical agent such as carbonyl chloride, sarin, or hydrocyanic acid.

Further, the blasting facility of this embodiment can be used for exploding a vessel containing a hazardous substance such as an organic halogen as well as the illustrated chemical bomb 100.

Figure 1:
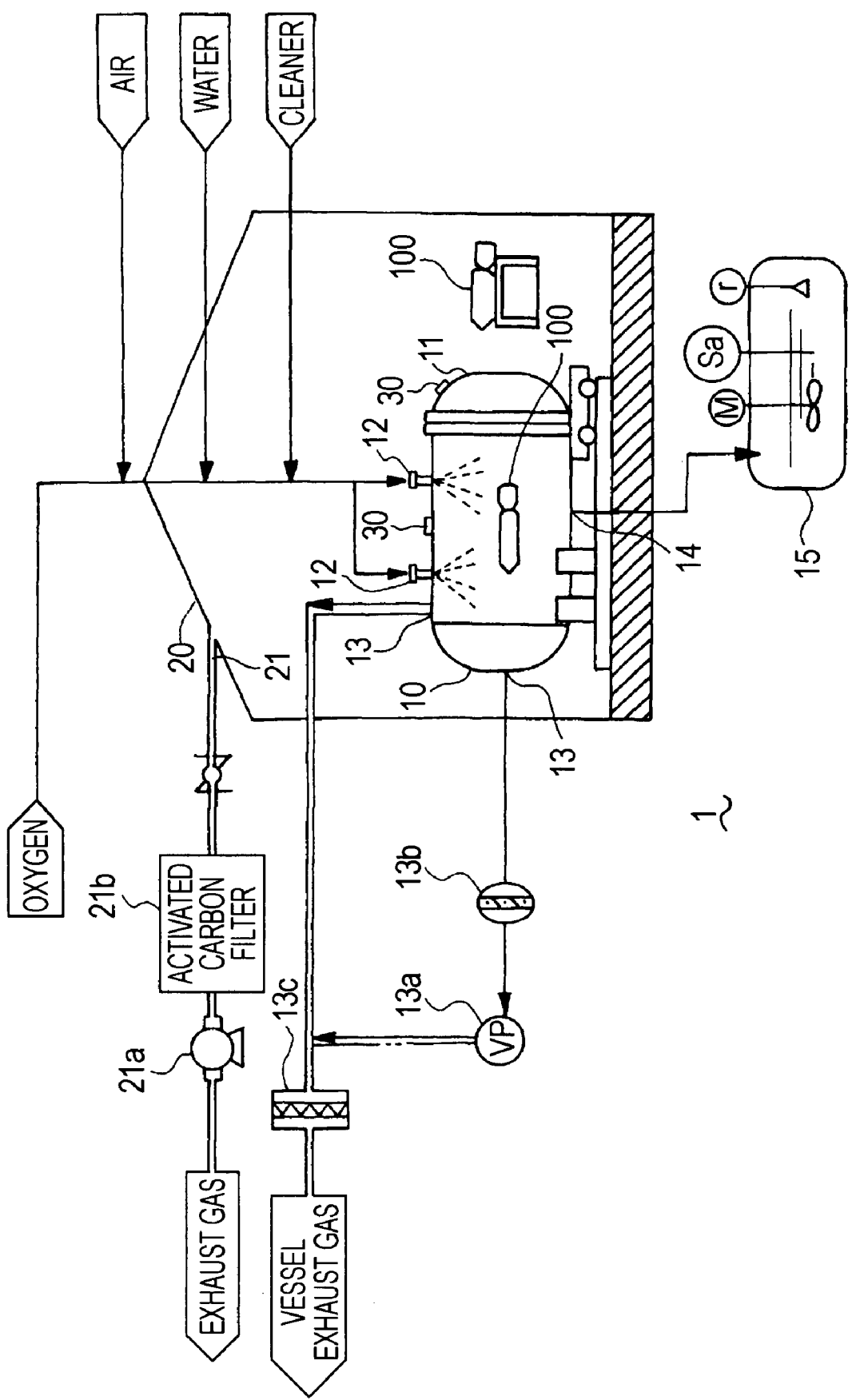
FIG. 1 is a block diagram of an overall structure of a blasting facility according to an embodiment of the present invention.

Referring next to FIG. 1, a blasting facility used outdoors as an example of a facility for exploding the above chemical bomb 100 or other such explosives is described. FIG. 1 is a schematic diagram of a schematic structure of the blasting facility.

A blasting facility 1 of FIG. 1 includes a blasting vessel 10, and a tent 20 accommodated in the blasting vessel 10 as main components.

The blasting vessel 10 has a bombproof structure made of iron or the like, and is designed to withstand an explosion pressure upon exploding an explosive such as the chemical bomb 100 therein. The blasting vessel 10 is a hollow vessel, which extends in one direction, and is placed in a horizontal position in its longitudinal direction.

A pressure-tight cover 11 removably attachable to a main body of the blasting vessel 10 is provided at one end of both ends of the blasting vessel 10 in the longitudinal direction. The pressure-tight cover 11 may be taken off the main body, making it possible to load the chemical bomb 100 or other such explosives into the blasting vessel 10. In this way, the chemical bomb 100 is set and fixed to the blasting vessel 10 by fixing means, not shown, and then the pressure-tight cover 11 is put on the main body to thereby seal the blasting vessel 10. In this state, the explosive is exploded.

Plural strain gauges 30 as a strain measuring apparatus are attached to the blasting vessel 10. The strain gauges 30 are connected to a high-speed data reading apparatus although not shown. The high-speed data reading apparatus is electrically connected to a computer, not shown. The computer includes a CPU as computing means (cumulative fatigue measuring means), a ROM, a RAM, and a hard disk drive as storage means (cumulative value storage means), and output means as a display or a printer.

Plural inlets 12 are provided in an upper portion of the blasting vessel 10. The inlets 12 are used for injecting oxygen into the blasting vessel 10 before explosion, and injection of the air, water, a washing agent, or the like into the blasting vessel 10 upon decontamination after the explosion.

Outlets 13 are provided in an upper portion of the blasting vessel 10 and a side portion opposing the pressure-tight cover 11. The outlets 13 are used to exhaust the air from the blasting vessel 10 before explosion through a filter $13b$ by a vacuum pump $13a$, and set the vessel under a reduced pressure or under vacuum. Alternatively, the outlets are used to remove exhaust air in vessels such as a vessel vent from the blasting vessel 10 after explosion through a filter $13c$.

Further, a drain outlet 14 is provided at the bottom of the blasting vessel 10. A decontaminated waste liquid is allowed to drain out to a treatment tank 15 through the drain outlet 14.

Incidentally, an igniter, not shown, is provided outside the blasting vessel 10 to ignite the chemical bomb 100 or other such explosives fixed into the blasting vessel 10. The igniter enables remote-controlled explosion.

Incidentally, a hard wall preferably surrounds the blasting vessel 10 to protect the tent 20 even if the chemical bomb 100 or other such explosives destroy the blasting vessel 10.

The tent 20 includes a not-shown door, and the chemical bomb 100 or other such explosives are loaded into the blasting vessel 10 or the tent 20 with the door opened. Further, the tent 20 is provided with an exhaust outlet 21. The exhaust outlet 21 is used to exhaust the air from the tent 20 through a filter $21b$ such as activated carbon by use of a blower $21a$.

In this way, in this embodiment, the chemical bomb 100 is exploded in the blasting facility 1 including at least the blasting vessel 10.

Next, an apparatus for estimating a residual life of the blasting vessel 10 used for operating the blasting facility 1 is described. The apparatus for estimating a residual life includes the plural strain gauges 30 attached to the blasting vessel 10, the high-speed data reading apparatus connected to the strain gauges 30, and a not-shown computer capable of acquiring data of the high-speed data reading apparatus.

Figure 3:
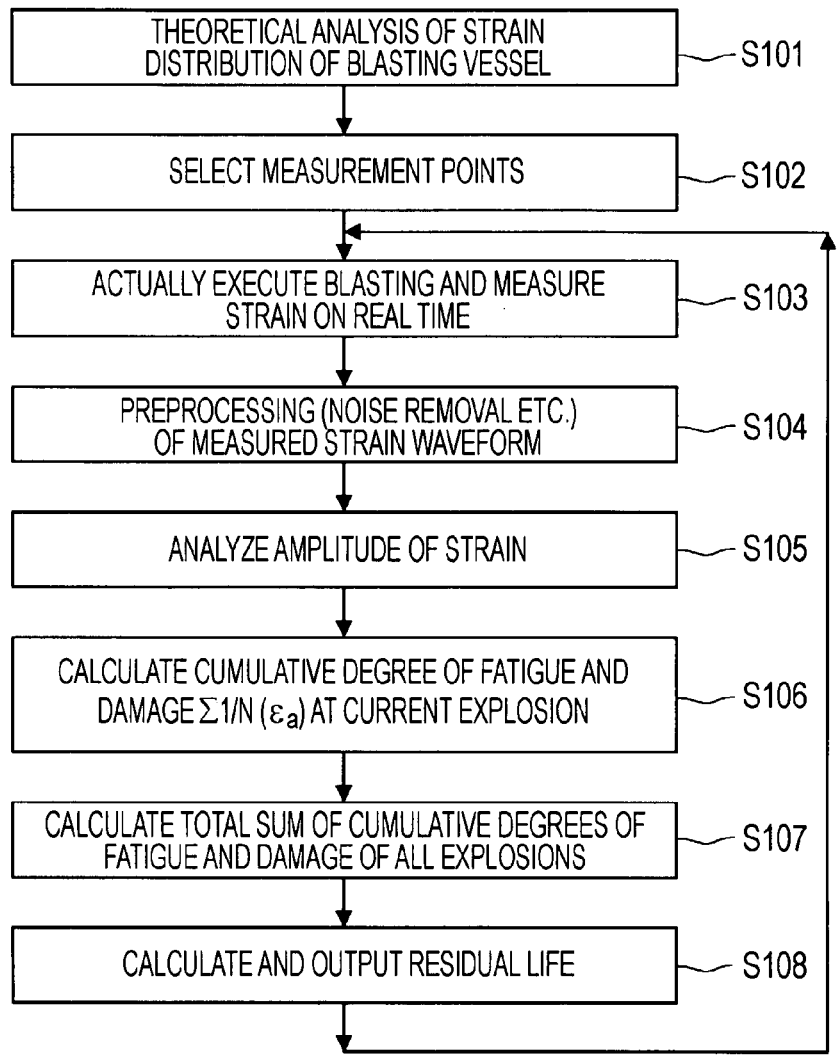
FIG. 3 is a flowchart showing how to manage a blasting vessel using an apparatus of estimating a residual life according to the embodiment of the present invention.

An estimating method using the apparatus for estimating a residual life is explained with reference to a flowchart of FIG. 3. Programs for performing processings of at least steps 103 to 108 of the flowchart are installed in the above computer and stored in storage means of the computer.

Figure 4:
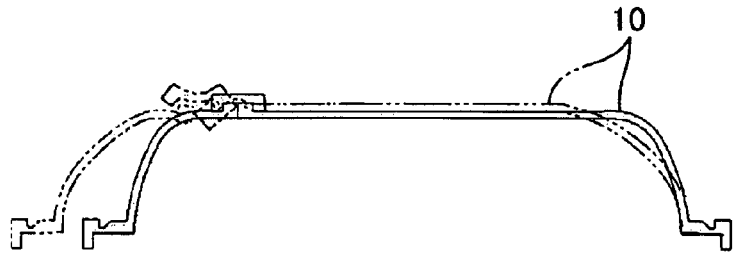
FIG. 4 illustrates an analysis example of a strain distribution of the blasting vessel.

In step 101 of the flowchart, a strain distribution upon explosion at a predetermined position in the blasting vessel 10 is theoretically analyzed. The theoretical analysis (simulation) may be performed by the computer connected to the strain gauges 30 or other computers. FIG. 4 is a sectional view of an upper half of the blasting vessel 10, which shows an analysis result of limited elements in the case where an internal pressure is applied to the blasting vessel 10.

In step 102 of the flowchart, characteristic points representative of a residual life of the blasting vessel 10 are selected as measurement points. The measurement points may be selected by various methods. Typically, a point considered to be shorter in residual life than any other portions of the blasting vessel 10 is selected as a measurement point.

The measurement point is positioned in an area where the strain gauge 30 can be attached in some cases or in area where the strain gauge 30 cannot be attached in other cases. The latter case, the case where the measurement point is positioned in an area where the strain gauge 30 cannot be attached is determined. If accurate measurement is difficult, the strain gauge 30 is attached to an attachable area near the measurement point, and a correlation between strain at the attached point of the strain gauge 30 and strain at the measurement point is theoretically analyzed and stored in correlation storage means such as a RAM of a computer.

Figure 5:
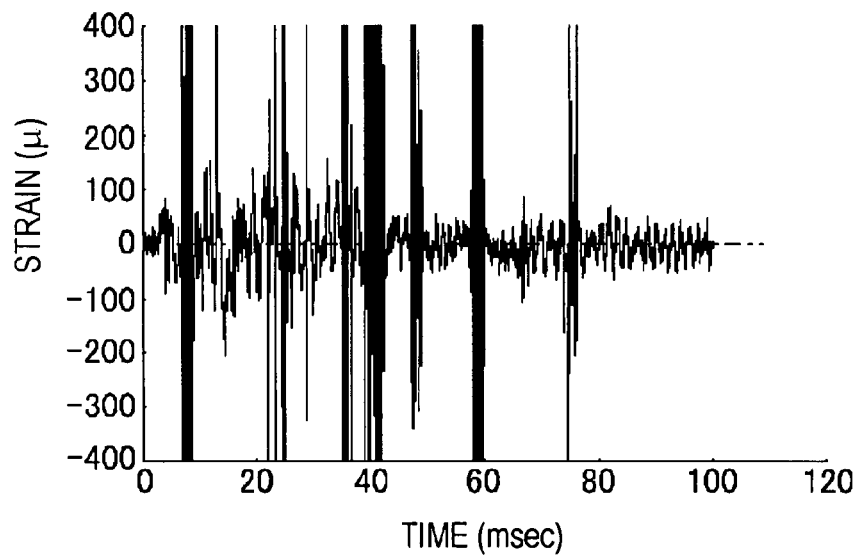
FIG. 5 is a graph of actual strain data measured with a strain gauge.

In step 103 of the flowchart, the chemical bomb 100 is actually set in a predetermined position in the blasting vessel 10, and explosion is executed in the vessel 10. Upon executing the explosion, the not-shown high-speed data reading apparatus reads and records strain waveform data output from the strain gauge 30. As the high-speed data reading apparatus, in this embodiment, an apparatus capable of sampling at a millisecond interval or less is used. The strain waveform data read with the high-speed data reading apparatus is a repetitive strain waveform at a high frequency as shown in FIG. 5, for example, and the waveform is transmitted to the computer.

Figure 6:
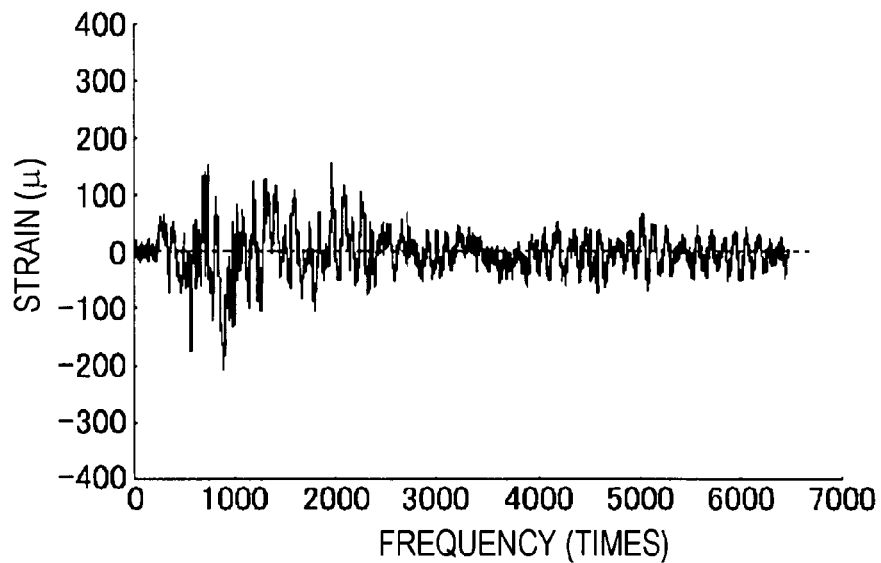
FIG. 6 is a graph of strain data after noise removal.

In step 104 of the flowchart, the computer immediately executes preprocessing such as noise removal on the obtained strain waveform. As a result, the waveform data of FIG. 5 is shaped into a waveform of FIG. 6. The preprocessing may be omitted if the data includes little noise. Further, the preprocessing may be performed on the high-speed data reading apparatus side, not the computer side.

In step 105 of the flowchart, the computer analyzes the obtained strain waveform, and reads an amplitude ($\epsilon_a$) of each strain at the measurement point. If the strain gauge 30 is attached to an area far from the measurement point, strain at the measurement point is determined on the basis of a value of strain measured by the stain gauge 30 and the correlation described in step 102, and an amplitude of each strain is measured as described above.

In step 106 of the flowchart, the computer calculates the degree of fatigue damage of the strain amplitude $\epsilon_a$ on the basis of an allowable number of explosions N, which is determined by a fatigue curve of a material relative to each strain amplitude $\epsilon_a$. In addition, the computer calculates cumulative degree of fatigue damage up to current explosion, as the total sum of the degrees of fatigue damage relative to all strain amplitudes. The fatigue curve is stored in advance by the computer.

In step 107 of the flowchart, the cumulative degree of fatigue damage calculated in step 106 is added to a cumulative value stored in a RAM as the cumulative value storage means of the computer, and the thus-added cumulative degree of fatigue damage is restored.

In step 108 of the flowchart, the computer further calculates a residual life of the blasting vessel 10 from the cumulative value and displays the calculation result on a display.

In the apparatus for estimating a residual life of this embodiment, the processings of steps S103 to S108 are performed on the computer every explosion. As a result, every explosion shortens a residual life on the display little by little. This display facilitates scheduling for testing the blasting vessel 10 or the like or for replacing the blasting vessel 10. Upon the replacement of the blasting vessel 10, the cumulative value is reset to zero in accordance with the replacement.

Figure 7:
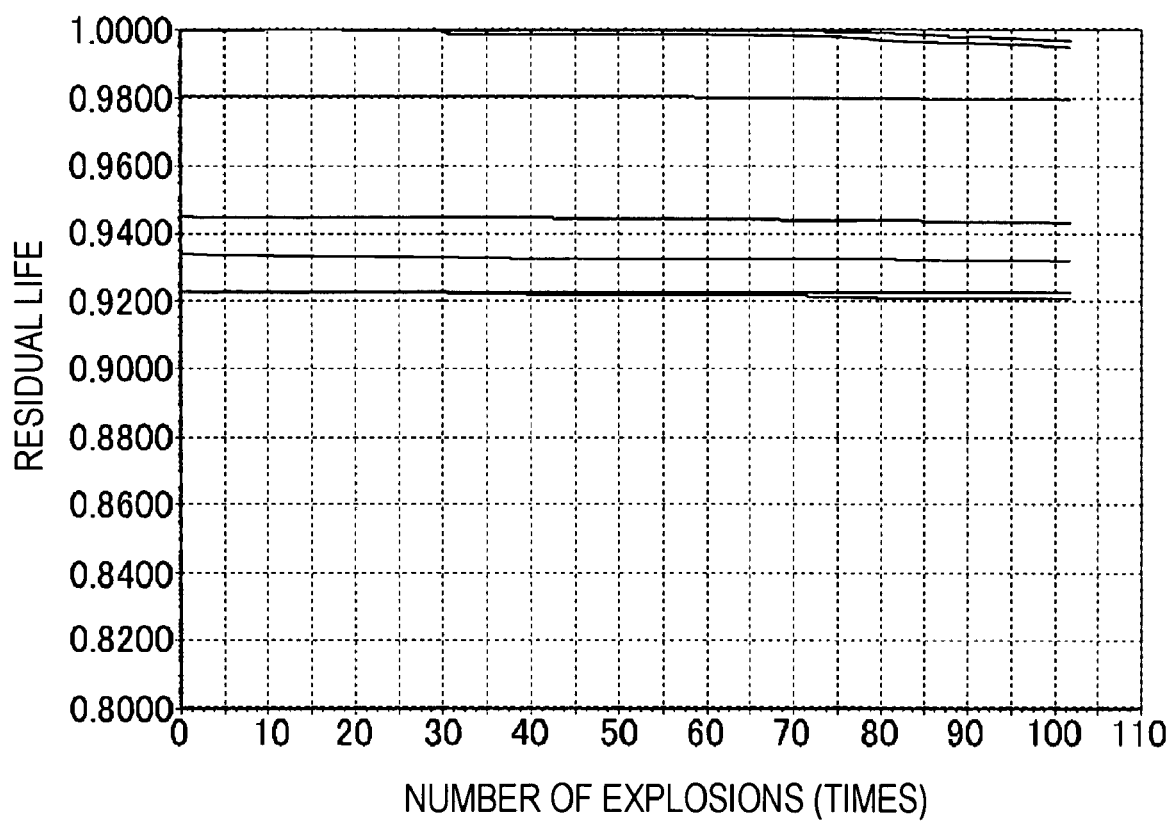
FIG. 7 is a graph showing a relation between the number of explosions and an estimated residual life.

FIG. 7 is a graph showing an example of a residual life estimated by the apparatus for estimating a residual life. The vertical axis of the graph represents a residual life. A value of the residual life is set to 1 for an unused new product and is set to 0 for an expired product. The horizontal axis of the graph represents the number of explosions.

As shown in FIG. 7, a curve of the estimated residual life tends to slope downwardly on the graph. That is, as a tendency thereof, the residual life is gradually shortened in inverse proportion to the number of explosions. The graph illustrates an example where a strength of explosive used is not constant. The degree to which the residual life shortens varies according to the change in strength. In the case where a strength of explosive is large, and a high load is applied to the blasting vessel 10, the residual life is relatively largely reduced.

The graph of FIG. 7 includes a curve of the residual life with an initial value of 1.0000. This curve represents data about the blasting vessel 10 subjected to many explosions even before estimation of the residual life with the computer. As for the data of the curve, a decrease in residual life due to fatigue in a period before the residual life estimation is separately calculated and reflected on the cumulative degree of fatigue damage (step 107), so an initial value of the curve is below 1.0000.

In the aforementioned blasting facility 1 of this embodiment, the degree of fatigue damage is quantitatively calculated per explosion, and the residual life is estimated on the basis of the calculation. Therefore, the facility 1 can run while the residual life of the blasting vessel 10 is constantly estimated. This facilitates appropriate scheduling of operations and prevents reduction in disposal capacity and increase in running cost.

The apparatus for estimating a residual life of the embodiment is set in the blasting vessel 10, and provided with a strain measuring apparatus (in the drawings, the strain gauge 30) for measuring a high-frequency repetitive strain per explosion, and the computer. The computer includes means for analyzing strain waveform data output from the strain measuring apparatus in each explosion, means for calculating the cumulative degree of fatigue damage due to a repetitive load at a high frequency applied to the blasting vessel 10 due to each explosion, and means for calculating a cumulative value of the degrees of fatigue damage from the start of use, and re-setting the value (steps 103 to 107). The processing of the computer enables accurate estimation of a residual life even if explosion conditions (for example, a strength of explosive) vary from one explosion to another.

Further, the above computer calculates an amplitude ea of each strain from the strain waveform data obtained with the strain measuring apparatus in each explosion, and compares the calculated value with the fatigue curve of a material for the blasting vessel 10 to thereby calculate the degree of fatigue damage resulting from the strain of each amplitude and add the calculated values to determine the cumulative degree of fatigue damage in each explosion (steps 105 and 106). Accordingly, the computer can appropriately calculate the cumulative degree of fatigue and accurately estimate a residual life.

Further, the computer includes means for storing a correlation such as a RAM for storing a level of strain at an attachable area of the strain gauge 30 and a level of strain at a measurement point if the strain gauge cannot be attached to a particular area including the measurement point, and calculates the strain at the measurement point on the basis of the stored correlation to determined the cumulative degree of fatigue damage. Therefore, it is possible to appropriately calculate the cumulative degree of fatigue damage with a simple structure. In particular, if the strain gauge 30 is attached near the measurement point, a measurement accuracy for the strain at the measurement point is high.

Further, the apparatus for estimating a residual life of this embodiment quantitatively estimates a residual life (steps 103 to 108 of FIG. 3) per explosion, and includes output means for immediately outputting the estimation result such as a display (step 108). That is, the apparatus for estimating a residual life immediately recalculates a residual life per explosion and displays the recalculated value. Accordingly, an operator can manage operations while checking a residual life all the time.

The residual life may be expressed in any other way with no particular limitation. The residual life may be expressed by numerical values of 0 to 1 as described above or in percentage of 0 to 100%, for example. The residual life may be displayed on the display in numerical values or may be visually displayed as a bar graph or the like. Further, a printer may print out the residual life per explosion.

The apparatus for estimating a residual life of the present invention can be used for exploding a vessel containing a hazardous substance such as an organic halogen as well as the illustrated chemical bomb 100. Further, the apparatus for estimating a residual life of FIG. 1 is placed outdoors, but the present invention is applicable to a facility where a pressure-tight vessel containing an explosive air-tightly and buried in the ground, and the explosion is executed under the ground.

The invention claimed is:

1. An apparatus for estimating a residual life of a blasting vessel in which an object to be treated is exploded, comprising:
 means for quantitatively evaluating the degree of fatigue damage of the blasting vessel upon each explosion; and,
 means for calculating an estimated value of residual life of the blasting vessel on the basis of the evaluation,
 wherein the means for quantitatively evaluating the degree of fatigue damage of the blasting vessel includes:
 a strain measuring apparatus for measuring a high-frequency repetitive strain caused in the blasting vessel due to the explosion upon each of explosions, the apparatus being set in the blasting vessel;
 cumulative fatigue calculating means for analyzing strain waveform data obtained with the strain measuring apparatus in each of the explosions to calculate cumulative degree of fatigue damage due to a repetitive load at a high frequency, which is applied to the blasting vessel by the explosion, at the current explosion; and
 cumulative value storage means for storing a cumulative value of the cumulative degree of fatigue damage from start of use.

2. A blasting facility, comprising:
 a blasting vessel in which an object to be treated is exploded; and
 the apparatus for estimating a residual life of a blasting vessel according to claim 1.

3. The apparatus for estimating a residual life of a blasting vessel according to claim 2, wherein the cumulative fatigue calculating means extracts a strain amplitude from the strain waveform data obtained with the strain measuring apparatus in each of the explosions, and compares the extracted strain amplitude with a fatigue curve of a material for the blasting vessel to calculate and add degrees of fatigue damage applied to the blasting vessel by strain of the strain amplitude to calculate the cumulative degree of fatigue damage upon the current explosion.

4. The apparatus for estimating a residual life of a blasting vessel according to claim 2, further comprising:
 correlation storage means for storing a correlation between a level of strain in a portion where the strain measuring apparatus is attached and a level of strain in a predetermined portion other than the attached portion,
 wherein the cumulative fatigue calculating means calculates strain in the predetermined portion on the basis of waveform data obtained with the strain measuring apparatus and the correlation stored in the correlation storage means, and calculates the cumulative degree of fatigue damage at the predetermined portion on the basis of the strain.

5. The apparatus for estimating a residual life of a blasting vessel according to claim 4, wherein the strain measuring apparatus is attached near the predetermined portion.

6. The apparatus for estimating a residual life of a blasting vessel according to claim 1, further comprising:
 output means capable of outputting an estimated value of a residual life for each of the explosions.

7. A method of estimating a residual life of a blasting vessel in which an object to be treated is exploded, comprising:
 quantitatively evaluating the degree of fatigue damage of the blasting vessel upon each explosion; and
 estimating a residual life of the blasting vessel on the basis of the evaluation,
 wherein the quantitatively evaluating the degree of fatigue damage of the blasting vessel includes:
 measuring a high-frequency repetitive strain caused in the blasting vessel due to the explosion upon each of explosions; and
 analyzing strain waveform data obtained with the strain measuring apparatus in each of the explosions to calculate cumulative degree of fatigue damage due to a repetitive load at a high frequency, which is applied to the blasting vessel by the explosion, at the current explosion; and
 the estimating a residual life includes calculating an estimated value of a residual life of the blasting vessel on the basis of a cumulative value of the cumulative degree of fatigue damage from start of use.

8. The method of estimating a residual life of a blasting vessel according to claim 7, wherein the calculating cumulative degree of fatigue damage includes extracting a strain amplitude from the strain waveform data obtained with the strain measuring apparatus in each of the explosions, and comparing the extracted strain amplitude with a fatigue curve of a material for the blasting vessel to calculate and add degrees of fatigue damage applied to the blasting vessel by strain of the strain amplitude to calculate the cumulative degree of fatigue damage upon the current explosion.

9. The method of estimating a residual life of a blasting vessel according to claim 7, further comprising:
 previously determining a correlation between a level of strain in a portion where the strain measuring apparatus is attached and a level of strain in a predetermined portion other than the attached portion,
 wherein the calculating cumulative degree of fatigue damage includes calculating strain in the predetermined portion on the basis of waveform data obtained with the strain measuring apparatus and the correlation, and calculating the cumulative degree of fatigue damage at the predetermined portion on the basis of the strain.

10. The method of estimating a residual life of a blasting vessel according to claim 8, further comprising:
 previously determining a correlation between a level of strain in a portion where the strain measuring apparatus is attached and a level of strain in a predetermined portion other than the attached portion,
 wherein the calculating cumulative degree of fatigue damage includes calculating strain in a predetermined portion on the basis of waveform data obtained with the strain measuring apparatus and the correlation, and calculating the cumulative degree of fatigue damage at the predetermined portion on the basis of the strain.

* * * * *